United States Patent [19]

Aralis et al.

[11] Patent Number: 4,744,657

[45] Date of Patent: May 17, 1988

[54] METHOD AND RECORD FOR CALIBRATION OF A SPECTROPHOTOMETER

[75] Inventors: Frank M. Aralis, Irvine; Barry S. Master, Tustin, both of Calif.

[73] Assignee: Beckman Instruments, Inc., Fullerton, Calif.

[21] Appl. No.: 754,369

[22] Filed: Jul. 11, 1985

[51] Int. Cl.$^4$ ............................................. G01J 3/02
[52] U.S. Cl. .................................. 356/319; 364/498; 364/571
[58] Field of Search ............... 356/319, 323, 325, 326, 356/328, 300; 364/498, 526, 571

[56] References Cited

U.S. PATENT DOCUMENTS

| | | |
|---|---|---|
| 4,093,991 | 6/1978 | Christie, Jr. et al. ............ 364/498 X |
| 4,482,251 | 11/1984 | Saylor .............................. 364/498 X |
| 4,519,706 | 5/1985 | Morley et al. ...................... 356/319 |

FOREIGN PATENT DOCUMENTS

| | | |
|---|---|---|
| 0055686 | 5/1977 | Japan .................................. 356/319 |
| 2113831 | 8/1983 | United Kingdom ............... 356/319 |

OTHER PUBLICATIONS

Malone et al., *American Lab.* (USA), vol. 12, No. 6, Jun. 1980, pp. 76–81.

*Primary Examiner*—F. L. Evans
*Attorney, Agent, or Firm*—W. H. May; P. R. Harder; S. R. Markl

[57] ABSTRACT

A record of calibration data containing determined values required for accurate operation of a scientific instrument measuring transmissions or absorbance of light in analysis is provided. A method of maintaining and using the records generated by the instrument permits use of the instrument to determine which records are required for efficient and easy instrument usage.

3 Claims, 1 Drawing Sheet

METHOD AND RECORD FOR CALIBRATION OF A SPECTROPHOTOMETER

BACKGROUND

In a spectrophotometer, a beam of light of a selected wavelength or frequency is passed through a sample where some of the light is absorbed by the molecules comprising the sample. The light which passes through the sample is received by a light sensitive detector system such as a photometer. The less light energy that is absorbed by this sample results in more light being received by the light detector system. The detector system generates an electrical signal of the strength proportional to the intensity of the light it receives. The output of the light detector system, for example one utilizing a photomultiplier tube, is generally an analog current signal proportional to the light intensity received, which thus is proportional to the light transmittance of the sample. It is the light transmittance of the sample which is of interest in that it indicates light absorbance by the sample which can be used to determine sample composition.

The light detector system generally has an amplifier such as an operational amplifier to convert the analog current signal from the light detector to an analog DC voltage signal. The DC voltage signal is processed by additional electronics and applied to a display, such as a chart recorder, to provide a visual and/or permanent record of the sample light transmittance, i.e. absorbance (absorbance=1/transmittance) at a selected light wavelength or through a wavelength scan.

The additional electronics may comprise, for example, digital to analog converters for adjusting the offset and gain of the detector system amplifier(s) to obtain calibration of the instrument analysis function. Logarithmic conversion electronics are provided to convert light transmittance values measured by the light detector system to light absorbance values for direct interpretation of an analysis by a user. A resistor network may be provided through which the signal produced by the light detector system may be selectively altered to provide means for calibration of the electronics for reduced transmittance signals. This is accomplished by directing the detector output through a select resistor of the network and then to the log conversion electronics and to an analog to digital converter (ADC) to generate a digital calibration signal corresponding to incremental absorbance values. Once the signal level for incremental absorbance values has been calibrated, it can be used during sample analysis as a basis for interpolation by the computer to determine the actual light absorbance by a sample. Preferably, calibration of the electronics at light transmittance levels of 100, 10, 1, and 0.1 percent transmission of light are performed which correspond to selected absorbance values of 0A, 1A, 2A and 3A, respectively, due to the logarithmic relationship between transmission and absorbance. A schematic representation of forms of such calibration and signal electronics are shown in FIGS. 1 and 2. Such electronics and their usage are described in the following U.S. Pat. Nos., 4,436,994 of Van Vliet, et al., 4,310,243 of Brown, et al., 4,300,203 of Brown.

In order to obtain accurate performance of the spectrophotometer in analysis of a sample, it is necessary to perform calibration of the spectrophotometer at least each time a new wavelength of light is selected for analysis. This is a time consuming operation, and in particular can be a burden to a user for sample analysis utilizing more than a single light wavelength which is common to spectrophotometer users.

A need thus exists in the field of scientific instrumentation which utilizes varying wavelength monochromatic light for analysis purposes, to improve the ability and speed with which a user can calibrate his instrument to provide improved accuracy and reproducibility in its function by decreasing the time necessary for calibration so that the instrument is more readily available for use.

SUMMARY OF THE INVENTION

A record format and a method for its maintenance and use is provided for a scientific instrument utilizing selected wavelengths of light to obtain light transmission and absorbance measurements, which comprises a computer having memory means including random access capabilities (i.e. random access memory) for data storage. The calibration record comprises information of electronic calibration values for the detector and computation of systemsd of the instrument determined by the instrument when a calibration is performed. Acceleration record is generated for each wavelength of light utilized by the instrument within the memory capacity of the instrument computer. Nine individual values are incorporated in each record and generally computer memory is sufficient to maintain approximately ten individual records. The records are indexed in memory according to the wavelength of light associated with the calibration values.

Records of calibration values for the most recently used light wavelengths are retained in computer memory by the following method: (1) If a record exists for calibration data of the specified light wavelength in the computer memory, the calibration data for the most recently performed calibration replaces old information in the record; (2) If there is no current record for selected light wavelength, a record of calibration data is generated and entered into the computer memory in its properly indexed position where memory space remains within the computer memory; (3) If the computer memory is full when calibration is performed for a new wavelength of light, a record is generated of the calibration data for the new wavelength of light and the computer inspects the records held in memory to determine those most recently used, i.e. accessed by the computer during instrument usage. The least recently used record is removed from the memory and the record of calibration data for the new wavelength is entered into its appropriate indexed position.

The calibration record for a selected wavelength of light is automatically accessed and the included calibration values utilized to preset the instrument electronic system, when analysis at the respective wavelength is directed.

In this manner the instrument automatically saves the most recently used records of calibration information within the memory capacity of the comprised computer. This allows the user to tailor the instrument for operation and calibration to suit his needs. If the user never requires usage of more wavelengths of light than the computer has memory space to record the calibration information for the utilized wavelengths, recalibration of the instrument electronics will never be required unless the user desires to do so. Thus, the record of calibration information and the method of its retention

DEATILED DESCRIPTION OF THE INVENTION

Figure 1:
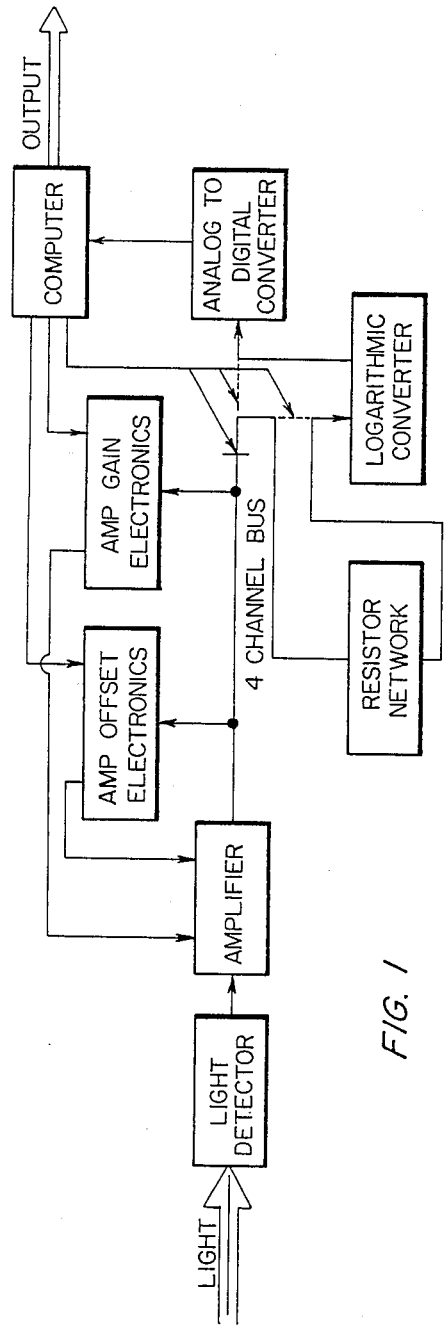
FIGS. 1 and 2 are schematic representations of the electronic calibration and signal processing systems as described in the Background of the Invention.
Figure 2:
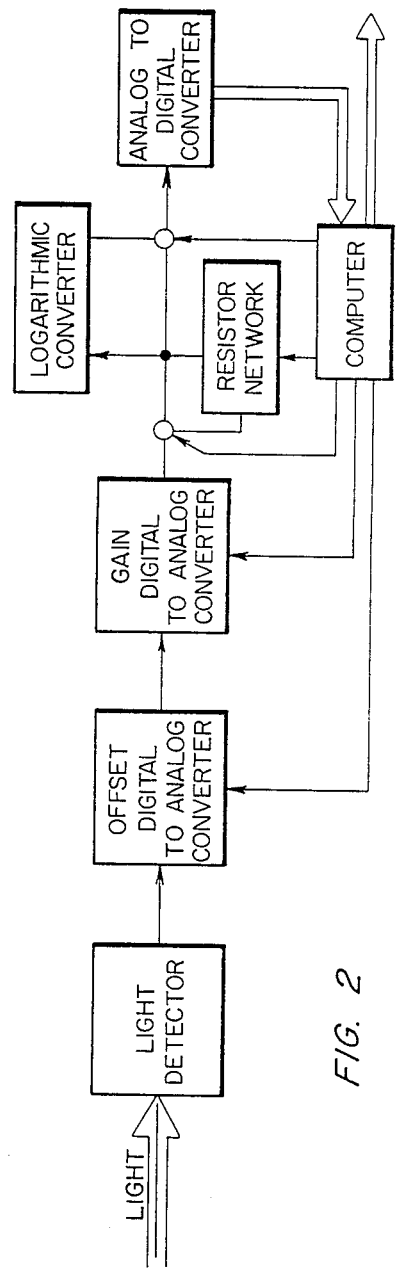

A record of calibration data, as described herein, preferably includes the following information:

1. Wavelength identification; the specific wavelength of monochromatic light for which the calibration data is applicable
2. Detector system amplifier offset value; this is the offset voltage required to drive the detector amplifier output to the proper signal voltage at zero light transmittance, i.e. where no light energy is received by the detector
3. Detector system amplifier gain value; this is the gain voltage required to drive the detector amplifier output to a selected output voltage at 100% light transmission, i.e. where all of the light energy generated by the instrument is received by the detector.
4. Processing electronics output for the absorbance values of 0A, 0.3A, 1A and 2A absorbanceunits, corresponding to 100%, 75%, 10% and 1% light transmittance as discussed; preferably each of these values is the count number of an analog to digital converter receiving the output of the logarithmic converter which processes the light detector signal as modified by the resistor network. These values incorporate four positions in the calibration record.
5. A light transmission reference at 100% light transmission; preferably this is the number of counts generated by the analog-to-digital converter receiving the output directly from the light detector without conversin by the logarithmic conversion electronics when the detector receives all the light energy generated by the instrument.
6. A light absorbance reference at 0% light absorbance; preferably this is the count number generated by analog to digital converter receiving the output of the light detector through the logarithmic conversion electronics when the detector receives all of the light energy generated by the instrument.

A record containing the above described values is maintained in the instrument for each individual wavelength of light utilized in the light transmission/absorbance analysis performed thereby. As many records as possible are retained in the memory of the computer controlling such an instrument and preferably ten records are includable to provide a sufficient range of calibration values for common usage of the instrument. Records are entered into the computer memory until allocated computer memory is completely used. The above described values are readjusted to the most recently determined calibration value if a record for the specific wavelength is included in memory once the computer memory contains the maximum number of records. Replacement of records when calibration is performed for a wavelength not currently included in memory, is as follows.

For example, when a user selects and calibrates the instrument at the wavelengths of 200 nm, 250 nm, 300 nm, 350 nm, 400 nm, 450 nm, 500 nm and 550 nm, each of the records of the calibration values for calibration of the instrument electronics at these wavelengths will be included in the computer memory. Reselecting any of these light wavelengths for analysis will cause the computer to automatically access the record for that specific wavelength and enter the calibration values into the electronic system of the instrument. Any changes required to the calibration values through recalibration of the instrument will be adjusted in the record for retention by the computer memory. Selecting a wavelength of light for analysis makes the corresponding calibration record, the most recently used record retained in memory.

As more calibrations are made at differing wavelengths of light, the space allocated to record storage in the computer memory becomes full. Once the memory is full, a calibration at a light wavelength not then stored within the computer memory, will force one of the records to be removed. That record will be the least recently used/accessed record contained in the computer memory as determinable by the computer. For example, if the user continued to calibrate the instrument for lightwave lengths of 600 nm and 650 nm, and the allocated computer memory was of a sufficient size to contain the preferred ten record positions, the computer memory would then be full with records of calibration data. The next calibration of a new light wavelength would require one of the records to be removed so that a record of the new calibration information could be stored in the computer memory. If, for instance, a light wavelength of 700 nm was selected and calibration of the instrument performed at this wavelength, a new calibration record would be generated and the current calibration record for, say for instance 200 nm which is the least recently used calibration record, would be removed. The 700 nm calibration record would then be entered into the computer memory in proper indexed position. If, between calibration of the instrument for the last 700 nm wavelength, readings had been taken at for instance a 200 nm, 300 nm, and 350 nm wavelength, and then the 700 nm wavelength calibration performed, the record of calibration data for a wavelength of 250 nm would be the least recently used record and this record would be removed for replacement by the new record of calibration data for the 700 nm wavelength. Again, it is the least recently used or accessed record for either calibration or sample analysis that is the record which is removed when a new record requires entry into the computer memory.

If the user uses a number of wavelengths no greater than the allocated space for records in the computer memory, the full range of records of calibration information required for instrument usage will be retained and continually updated as the instrument is used. Since a typical scientific instrument application uses less than ten wavelengths of light for analysis, the calibration of the instrument to determine the values held in the records is never required unless instrument performance indicates such is required and calibration is directed by the user. Automatic maintenance of calibration information in the calibration records and the designed retention of calibration records for the most recently used light wavelengths in determining transmission/absorbance information from the instrument, substantially reduces the time required of the user in instrument operation and improves accuracy and reliability of the instrument in analysis.

What is claimed is:

1. A method for obtaining calibration of a scientific instrument performing analysis through measurement of light transmission or absorbance at certain wavelengths of generated monochromatic light, said instrument being controlled by a computer or microprocessor having memory means for storing and accessing information, and electronic signal processing means including amplifiers responsive to calibration signals for generating an output responsive to said light measurement, comprising:

generating a plurality of records of calibration signal values by said computer for entry into said next computer memory, said computer memory storing the most recent record and retaining the next most recent n records used by said scientific instrument, and erasing all records ealier than n records upon introduction of a new record into computer memory for each wavelength of light measured, each record comprising a plurality of signals for reception by said electronic signal processing means which provide information of the following parameters:

(a) wavelength of light;
(b) amplifier offset value for a specified light wavelength;
(c) amplifier gain value for a specified light wavelength;
(d) a first processing means output for a first light transmission characteristic;
(e) a second processing means output for a second light transmission characteristic.

2. The method for obtaining calibration of claim 1 wherein generation of said record of calibration signals include signals which provide information of the following parameters:

(f) processing means output of a first light transmission characteristic indicating absorbance;
(g) processing means output of a second light transmission characteristic indicating absorbance.

3. The method for obtaining calibration of the scientific instrument of claim 1 wherein said generation of a record of calibration signals further includes a signal providing a parameter for reference of the processing means output when no light is absorbed prior to measurement.

* * * * *

UNITED STATES PATENT AND TRADEMARK OFFICE
CERTIFICATE OF CORRECTION

PATENT NO. : 4,744,657
DATED      : May 17, 1988
INVENTOR(S) : Frank M. Aralis and Barry S. Master It is certified that error appears in the above-identified patent and that said Letters Patent is hereby corrected as shown below:

Column 5, line 13      the word "next" should be deleted

Signed and Sealed this

Twenty-fifth Day of October, 1988

*Attest:*

DONALD J. QUIGG

*Attesting Officer*            *Commissioner of Patents and Trademarks*